(12) United States Patent
Joly et al.

(10) Patent No.: US 7,297,826 B2
(45) Date of Patent: Nov. 20, 2007

(54) METHOD FOR PRODUCING PHENYLALKANES USING A COMBINATION OF TWO CATALYSTS

(75) Inventors: Jean-François Joly, Lyons (FR); Patrick Briot, Pommier de Beaurepaire (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 535 days.

(21) Appl. No.: 10/495,773

(22) PCT Filed: Nov. 5, 2002

(86) PCT No.: PCT/FR02/03793

§ 371 (c)(1),
(2), (4) Date: May 17, 2004

(87) PCT Pub. No.: WO03/042137

PCT Pub. Date: May 22, 2003

(65) Prior Publication Data

US 2005/0010072 A1    Jan. 13, 2005

(30) Foreign Application Priority Data

Nov. 15, 2001   (FR) ................................. 01 14885

(51) Int. Cl.
  *C07C 2/66*   (2006.01)
(52) U.S. Cl. ........................ 585/467; 585/449; 585/455
(58) Field of Classification Search ................ 585/449, 585/467, 455
  See application file for complete search history.

(56) References Cited

U.S. PATENT DOCUMENTS 5,777,187 A    7/1998   Knifton

FOREIGN PATENT DOCUMENTS

WO    WO 97 47573    12/1997

*Primary Examiner*—Thuan Dinh Dang
(74) *Attorney, Agent, or Firm*—Millen, White, Zelano & Branigan, P.C.

(57) ABSTRACT

A process is described for producing phenylalkanes by alkylating at least one aromatic compound using at least one linear olefin containing 9 to 16 carbon atoms per molecule. The alkylation reaction is carried out in the presence of at least two different catalysts used in at least two distinct reaction zones. The selectivity for a monoalkylated products of the catalyst contained in the first reaction zone is lower than that for the catalyst contained in the second reaction zone located downstream of the first in the direction movement of the fluids.

18 Claims, 1 Drawing Sheet

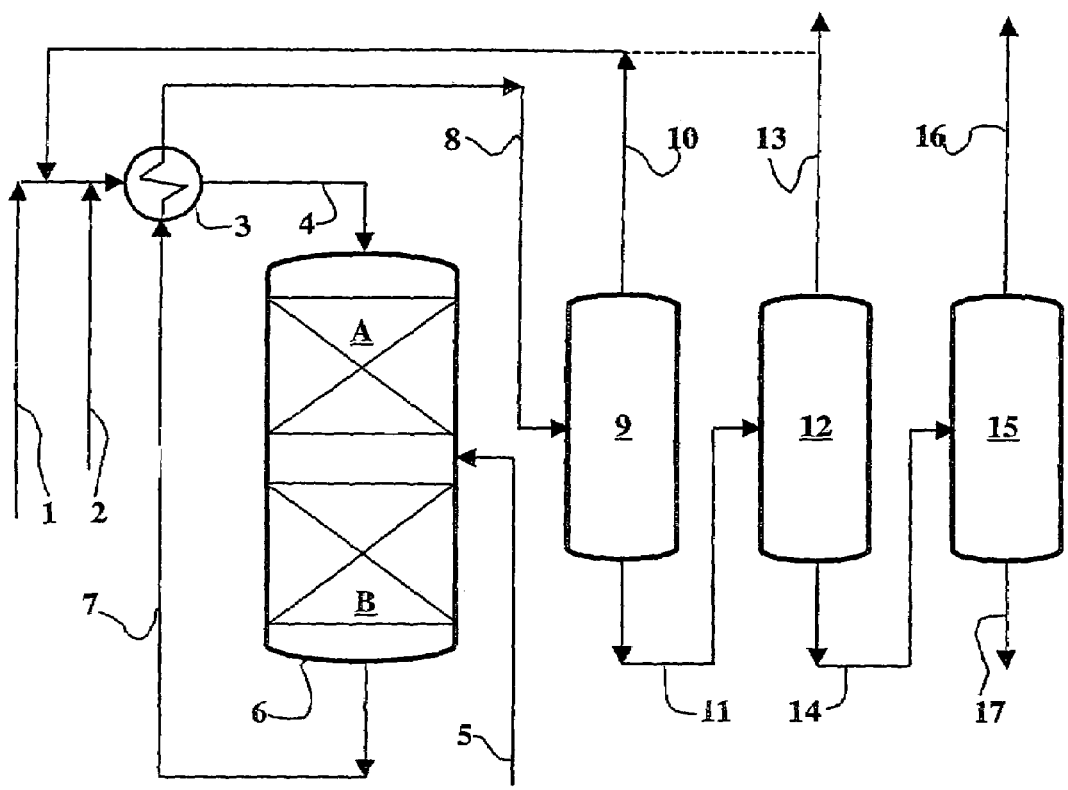

METHOD FOR PRODUCING PHENYLALKANES USING A COMBINATION OF TWO CATALYSTS

The present invention relates to the field of processes for producing phenylalkanes by alkylating benzene using at least one mono-olefin, usually linear, and generally containing 9 to 16 carbon atoms per molecule. The alkylation reaction is carried out in the presence of at least two different catalysts, used in at least two distinct reaction zones. The present invention allows the quantity of 2-phenylalkane isomer produced to be adjusted and modified depending on requirements while reducing the proportions of heavy polyalkylated compounds deriving from the alkylation reaction. In one non limiting example of application, the phenylalkanes obtained in accordance with the invention constitute precursors for formulating detergents after sulphonation, in particular certain biodegradable detergents.

Currently, bases for biodegradable detergents are largely derived from linear alkylbenzenes. Production of that type of compound is increasing steadily. In addition to their detergent power, one of the principal desired properties for such compounds, after a sulphonation step, is biodegradability. To ensure maximum biodegradability, the alkyl group must be linear and long and the distance between the sulphonate group and the terminal carbon of the linear chain must be a maximum. Thus, the most interesting benzene alkylation agents are constituted by linear $C_9$-$C_{16}$ olefins, preferably $C_{10}$-$C_{14}$.

Linear alkylbenzenes generally obtained by alkylating benzene using linear olefin(s) are usually prepared using two known processes. The first process described, for example, in Ullmann's encyclopedia ($5^{th}$ volume A25, page 766) uses hydrofluoric acid as the acid catalyst during the benzene alkylation step. The second process described, for example, in Ullmann's encyclopedia ($5^{th}$ volume A25, page 766) uses a Friedel-Crafts type catalyst, generally based on $AlCl_3$. Those two processes lead to the formation of 2-, 3-, 4-, 5- and 6-phenylalkane isomers. The principal disadvantage of those processes is connected to environmental constraints. The first process, based on the use of hydrofluoric acid, causes severe problems with safety and with waste treatment. The second process, based on the use of a Friedel-Crafts type catalyst, poses problems with discharges deriving from using such a catalyst. In that case, the effluents have to be neutralized with a basic solution at the reactor outlet. Further, the catalyst has to be separated from the reaction products; in both processes, this is difficult to carry out.

Such constraints explain the interest in developing a process for alkylating benzene with olefins, and more particularly with linear olefins in the presence of a solid catalyst.

The prior art essentially regards the use of catalysts with geometric selectivity properties leading to improved selectivity for 2- and 3-phenylalkanes. Said catalysts with geometric selectivity properties are generally constituted by zeolitic compounds as defined in the "Atlas of zeolite structure types" (W M Meier, D H Olson and Ch Baerlocher, $4^{th}$ revised edition, 1996, Elsevier) to which reference should be made in the present application. United States patent U.S. Pat. No. 4,301,317 describes a series of zeolites including cancrinite, gmelinite, mordenite, offretite and ZSM-12. The Applicant's French patent FR-B-2 697 246 shows that it is possible to use catalysts based on dealuminated Y zeolite. European patent EP-B1-0 160 144 describes the use of partially crystalline zeolites, in particular Y zeolites the crystallinity of which is between 30% and 80% while U.S. Pat. No. 5,036,033 describes the use of Y zeolites that are rich in ammonium cations. U.S. Pat. No. 4,301,316 shows that the nature of the catalyst has a direct influence on the composition of the different phenylalkane isomers produced. The selectivities for phenylalkane isomers after reacting 1-dodecene with benzene in the presence of a variety of catalysts, as given in the prior art, are shown in Table I. It clearly shows that for a catalyst with a given structure, the proportion of 2-phenylalkane isomer essentially results from the intrinsic characteristics of the catalyst. Using an HF catalyst results in a proportion of 20% of 2-phenylalkane, while using ZSM-12 leads to a proportion of 92% of 2-phenylalkane.

TABLE 1

| catalyst | 2-φ (%) | 3-φ (%) | 4-φ (%) | 5-φ (%) | 6-φ (%) |
|---|---|---|---|---|---|
| ZSM-12 | 92 | 8 | 0 | 0 | 0 |
| mordenite | 85 | 15 | 0 | 0 | 0 |
| offretite | 79 | 14 | 5 | 1 | 1 |
| ZSM-4 | 57 | 25 | 8 | 5 | 5 |
| beta | 57 | 18 | 10 | 7 | 8 |
| linde L | 40 | 18 | 16 | 15 | 11 |
| ZSM-38 | 37 | 19 | 13 | 14 | 16 |
| ZSM-20 | 51 | 21 | 11 | 9 | 8 |
| REY | 25 | 20 | 18 | 19 | 18 |
| HF | 20 | 17 | 16 | 23 | 24 |
| AlC13 | 32 | 22 | 16 | 15 | 15 |

U.S. Pat. No. 6,133,492 discloses a process for producing linear alkylbenzenes resulting in a high selectivity for 2-phenylalkane. This prior process uses two reactors in series: the first reactor contains a catalyst based on mordenite zeolite containing fluorine and the second reactor contains a second alkylation catalyst the selectivity for 2-phenylalkane of which is lower than that of the catalyst based on fluorinated mordenite. The second alkylation catalyst is preferably selected from the group formed by fluorinated silica-alumina, clays containing fluorine and aluminium chloride. Even though it results in a high selectivity for 2-phenylalkane, this prior art process is not satisfactory as regards the distribution of the products obtained at the outlet from the second reactor: dialkylated products and heavy products with a plurality of linear chains on the benzene ring are produced in non negligible quantities, which limits the proportion of desired mono-alkylated compounds in the final composition.

The present invention proposes to provide a process for alkylating aromatic compounds, preferably benzene, using linear olefin(s) containing 9 to 16 carbon atoms per molecule, more particularly 10 to 14 carbon atoms per molecule, which can not only allow adjustment of the selectivity for 2-phenylalkane to a desired level but can also increase the proportion of mono-alkylated products produced, i.e., containing only a single linear chain on the benzene ring, and as a result lead to the production of fewer di-alkylated compounds and heavy compounds.

The process of the invention employs at least two distinct reaction zones each containing at least one catalyst, the characteristics of which are given below. The process of the present invention uses at least two catalysts, the catalysts used in each of said reaction zones being different from each other and the selectivity for monoalkylated products of the catalyst contained in the first reaction zone being lower than that of the catalyst contained in the second reaction zone located downstream of the first in the direction of fluid movement.

BRIEF DESCRIPTION OF THE DRAWING

The FIGURE represents the invented process using a serial two beds of reaction.

Advantageously, at least one of said catalysts contained in said distinct reaction zones comprises at least one zeolite. Particularly advantageous zeolites for used in the process of the invention are selected from the group formed by zeolites with structure types FAU, MOR, MTW, OFF, MAZ, BEA and EUO. Y zeolite with structure type FAU, mordenite with structure type MOR, ZSM-12 zeolite with structure type MTW, offretite with structure type OFF, ZSM-4 zeolite with structure type MAZ and beta zeolite with structure type BEA are particularly preferred. REY zeolite is a faujasite type zeolite, which is highly acidic, and can also be used.

In a particular implementation of the invention, in one of the reaction zones a catalyst containing a Y zeolite is used. Clearly, depending on its nature and characteristics, in particular in terms of selectivity for monoalkylated compounds, of the other catalyst used in combination with the catalyst based on Y zeolite and also depending on the desired proportion of 2-phenylalkane, the catalyst based on Y zeolite will occupy either the first reaction zone or the second reaction zone located downstream of the first zone in the fluid movement direction. The Y zeolite present in one of the catalysts used in any of said reaction zones is advantageously a dealuminated Y zeolite, with an overall Si/Al atomic ratio of more than 4, preferably in the range 8 to 70 and more preferably in the range 15 to 25, and containing no aluminium species outside the crystalline lattice. Dealuminated Y zeolites and their preparation are known: as an example, reference should be made to the disclosure in U.S. Pat. No. 4,738,940. Dealuminated Y zeolite is used as a mixture with a binder or a matrix generally selected from the group formed by clays, aluminas, silica, magnesia, zirconia, titanium oxide, boron oxide or any combination of at least two of said oxides such as silica-alumina or silica-magnesia. All known methods for agglomerating and forming are applicable, examples being extrusion, pelletization or drop coagulation. In a particular implementation, the process of the invention uses a catalyst based on a dealuminated Y zeolite, said catalyst generally containing 1% to 100%, preferably 20% to 98% and more preferably 40% to 98% by weight of said dealuminated Y zeolite and 0 to 99%, preferably 2% to 80%, more preferably 2% to 60% by weight of a matrix or binder. In a particular implementation of the invention, the Y zeolite used can also be an acidic HY zeolite characterized by different specifications and in particular an overall Si/Al atomic ratio of more than 4, preferably in the range 8 to 70, and more preferably in the range 15 to 25, with a sodium content of less than 0.25% by weight, a lattice parameter for the unit cell of less than $24.55 \times 10^{-10}$ m, preferably in the range $24.21 \times 10^{-10}$ m to $24.39 \times 10^{-10}$ m, a specific surface area determined using the BET method of more than about 300 m$^2$/g, preferably more than about 450 m$^2$/g, and a water vapour adsorption capacity at 25° C. for a partial pressure of 3.46 millibars (mbar) of more than about 0.5%, preferably more than about 3%.

The proportion of extra-lattice aluminium species in the dealuminated Y zeolite is very small or even zero, and so no signal attributable to such species can be detected either by $^{27}$Al nuclear magnetic resonance using magic angle rotation, nor by infrared spectroscopy in the hydroxyl group region. More quantitatively, the ratio of the intensity of the signals corresponding to extra-lattice (ex-framework) aluminium species to the intensity of signals corresponding to the aluminium species in the framework is less than 0.05, regardless of the characterization technique used.

The overall Si/Al atomic ratio is generally measured by chemical analysis. When the quantity of aluminium is low, for example less than 2%, an atomic adsorption spectrometric assay method is preferably used.

The lattice parameter can be calculated from the X ray diffraction diagram, using the method described in American Standard ASTM D 3942-80. to carry out this calculation, the crystallinity of the product should be sufficiently high.

The specific surface area is, for example, determined by measuring the nitrogen adsorption isotherm at the temperature of liquid nitrogen and calculated using the conventional BET method. Before measurement, the samples are pre-treated at 500° C. in a stream of dry nitrogen.

Water take-up percentages (or water vapour adsorption capacity) are determined, for example, using a conventional gravimetric apparatus. The sample is pre-treated at 400° C. under low vacuum, then heated to a stable temperature of 25° C. Water is then admitted at a pressure of 3.46 mbar, corresponding to a $P/P_0$ ratio of about 0.10 (ratio between the partial pressure of water admitted into the apparatus and the saturated vapour pressure of water at 25° C.).

Y zeolites are generally produced from a NaY zeolite using a suitable combination of two basic treatments: a) a hydrothermal treatment which combines temperature and water vapour partial pressure, and b) an acid treatment preferably carried out using a strong concentrated mineral acid. Generally, the NaY zeolite from which the Y zeolite is prepared that is used in the process of the invention has an overall Si/Al atomic ratio in the range about 1.8 to 3.5; it is convenient to first reduce the sodium content to less than 3% by weight, preferably to less than 2.5%. The sodium content can be reduced by ion exchange of the NaY zeolite with ammonium salt solutions (nitrate, sulphate, oxalate, etc.), with an ammonium concentration between 0.01 and 10 N, at a temperature in the range 10° C. to 180° C. (optionally with exchange under autogenous pressure) for a period of more than about 10 minutes. The NaY zeolite also generally has a specific surface area in the range about 750 to 950 m$^2$/g.

In a further particular implementation of the invention, a catalyst containing a mordenite zeolite is used in one of the reaction zones. Clearly, depending on its nature and characteristics, in particular its selectivity for monoalkylated compounds, the other catalyst used in combination with the catalyst based on mordenite zeolite and also depending on the desired proportion of 2-phenylalkane, the catalyst based on mordenite zeolite will occupy either the first reaction zone or the second reaction zone located downstream of the first zone in the fluid movement direction. The mordenite zeolite present in one of the catalysts used in any of said reaction zones is advantageously a non fluorinated mordenite zeolite. It generally has an overall Si/Al atomic ratio in the range 6 to 100, preferably in the range 15 to 60 and more preferably in the range 20 to 50, with a sodium content of less than 1000 ppm by weight, preferably less than 500 ppm, a microporous volume, measured by adsorption of nitrogen at 77K in a nitrogen partial pressure of 0.19, of more than 0.160 cm$^3$ (liquid)/g, preferably more than 0.180 cm$^3$ (liquid)/g. In a first stage, preparing the catalyst based on a zeolite with structure type MOR, preferably mordenite zeolite, consists of eliminating the major portion of the sodium cations present in said zeolite and replacing them with protons and then in a second stage optimizing the overall Si/Al and framework ratios. To eliminate the major portion of the sodium cations, it is possible to carry out one or more series of exchanges in solutions of ammonium salts (ammonium chloride, nitrate or sulphate, for example) in a solution with a concentration in the range 0.01 to 15 N or in solutions of a variety of acids (HCl, $H_2SO_4$, $HNO_3$ of low normality) at a temperature in the range 10° C. to 180° C. Said exchange can optionally be carried out under autogenous pressure for a period of more than about 10 minutes.

To obtain the desired overall and framework Si/Al ratios, dealumination techniques that are known to the skilled person can be used, for example direct acid attack of the sodium form of the mordenite (NaMOR) partially exchanged or not partially exchanged with $H^+$ or $NH_4^+$ ions (HMOR or $NH_4$MOR respectively), calcining of the HMOR or $NH_4$MOR form optionally in the presence of steam preferably being followed by a chemical treatment of the acid attack type. Acid attack consists of at least one treatment in acid solutions of various natures (HCl, $HNO_3$, $H_2SO_4$, HF etc) at temperatures in the range 50° C. to 150° C. (optional attack under autogenous pressure). The acid concentration s are in the range 0.5 to 15 N, preferably in the range 5 to 12 N. The volume ratios of solution per weight of dry solid are in the range 3 to 20 $cm^3/g$, advantageously in the range 3 to 7 $cm^3/g$. The treatment period is at least 10 minutes. To achieve the desired specifications, a limited number of acid attacks can be carried out under severe conditions or a larger number of attacks can be carried out under moderate conditions. Direct acid treatment on a mordenite can also eliminate the major portion of the sodium cations and thus avoid an initial cation exchange step. Heat treatment in the presence of steam normally consists of calcining carried out at a temperature of more than 350° C., preferably more than 500° C., for a period of at least 10 minutes, in an atmosphere containing at least 1% steam, preferably at least 10% steam. The acid attack which optionally follows calcining is carried out under the same conditions as the acid attack described above.

According to the present invention, the prepared mordenite can be used alone or as a mixture with a binder or a matrix generally selected from the group formed by clays, aluminas, silica, magnesia, zirconia, titanium oxide, boron oxide and any combination of at least two of these compounds, preferably silica-alumina or silica-magnesia. All known methods for agglomeration and forming are applicable, such as extrusion, pelletization, drop coagulation or spray drying. In a particular implementation of the invention, a catalyst based on a mordenite is used, said catalyst generally containing 1% to 100%, preferably 20% to 98% and more preferably 40% to 98% by weight of said mordenite and 0 to 99%, preferably 2% to 80% and more preferably 2% to 60% by weight of a matrix or a binder.

To carry out the process of the invention, it may also be highly advantageous to use in each of said distinct reaction zones at least one catalyst containing at least one zeolite (zeolitic catalyst). In accordance with the invention, the zeolites present in each of the zeolitic catalysts differ from each other in their structure type and/or in the chemical composition of their crystalline framework. As an example, it is possible to use two zeolitic catalysts each containing a zeolite with a different structure type. It is also possible to use two zeolitic catalysts each containing a zeolite with an identical structure type but with a different chemical composition for the crystalline framework, i.e., with a different Si/Al ratio, for example, so that each of the zeolitic catalysts has a different selectivity for monoalkylated compounds, for example after a different maturation treatment. Any combination of two zeolitic catalysts differing by their structure type and/or a chemical composition of the crystalline framework for the zeolites used and in which the selectivity for monoalkylated compounds of the catalyst used in the first zone is lower than that of the catalyst used in the second zone can be envisaged for carrying out the process of the invention to obtain the desired selectivity for 2-phenylalkane and an optimum selectivity for monoalkylated compounds. In this implementation of the invention, in which at least two zeolitic catalysts are combined, a particularly preferred combination is a combination of a catalyst based on a zeolite with structure type FAU, in particular Y zeolite, and a catalyst based on a zeolite with structure type MOR, in particular mordenite zeolite, the zeolite with structure type FAU being contained in the first catalyst, i.e., in the catalyst present in the first reaction zone, and the zeolite with structure type MOR being contained in the second catalyst, i.e., in the second reaction zone located downstream of the first in the direction of fluid movement. The Y and MOR zeolites contained in each of the zeolitic catalysts have similar physico-chemical properties to those described above. By means of this combination of Y and mordenite zeolites, it is possible to adjust the proportion of 2-phenylalkane at the outlet from the process between about 25% by weight and about 85% by weight.

The process of the present application can be carried out in a single reactor, generally a fixed bed reactor, in which the reaction zones containing the catalysts are located, or it can be carried out in reactors in series, each containing a single catalytic zone containing one catalyst type. This second configuration will usually be preferred as it can generally better accommodate the properties and optimum reaction conditions associated with each catalyst, for example by adjusting the temperatures of the two reactors independently.

In one implementation of the process of the invention, the olefin(s) is/are mixed with the aromatic compound(s) upstream of the first reaction zone.

In a further preferred implementation of the process of the invention, a first fraction of the olefin(s) is mixed with the aromatic compounds upstream of the first catalytic zone and a second fraction of the olefin(s) is mixed with at least a portion of the effluents from the first reaction zone. Preferably, the quantity of olefin(s) contained in said first fraction is such that substantially all of said olefin(s) is consumed in the first reaction zone.

In general, the alkylation reaction is followed by at least one step for separating excess reactants. It is also advantageously followed by at least one step for separating the monoalkylated compounds from the reaction.

In a non limiting application of the process of the invention, benzene is reacted with a feed comprising at least one linear olefin containing 9 to 16 carbon atoms per molecule, preferably 10 to 14 carbon atoms per molecule, the feed possibly containing paraffins. All of the benzene can be introduced into the inlet to the first reaction zone containing the first catalyst, the mixture containing the linear olefins can be introduced in its entirety into the inlet to the first zone, or preferably fractionated into at least two portions, one being introduced to the inlet to the first catalyst zone, the other being introduced to the inlet to the second zone, located downstream of the first in the direction of fluid flow. When a single reactor comprising a plurality of reaction zones is used, side injection can be carried out into the reactor, for example, into a zone located between two reaction zones.

At the outlet from the reactor or reactors, i.e., the zone containing the second reactor, the product obtained is generally fractionated to recover separately a first fraction comprising unconverted benzene, a second fraction comprising at least one unconverted linear $C_9$-$C_{16}$ olefin (preferably $C_{10}$-$C_{14}$) and the paraffins that may have initially been present in the feed, a third fraction comprising 2-, 3-, 4-, 5- and 6-phenylalkanes and a fourth fraction comprising at least one polyalkylbenzene (or polyalkylbenzene fraction), which can optionally be recycled at least in part to one of the two reaction zones where it reacts with benzene in contact with the catalyst present in the catalytic zone concerned, in order to be at least partially transalkylated (transalkylation reaction) and a mixture of 2-, 3-, 4-, 5- and 6-phenylalkanes is recovered.

Similarly and preferably, the second fraction comprising at least one unconverted linear $C_9$-$C_{16}$ (normally $C_{10}$-$C_{14}$) olefin is recycled at least in part to one of the two reaction zones.

The operating conditions applied to the two reaction zones are, of course, selected by the skilled person as a function of the structure of the catalyst, the total pressure being substantially the same (with the exception of pressure drops) for the two reaction zones. The two reaction zones are operated at a temperature that is normally less than 400° C., preferably less than 300° C. and more preferably less than 250° C. and at a pressure of 1 to 10 MPa, with a flow rate of liquid hydrocarbons (space velocity) of about 0.5 to 50 volumes per volume of catalyst per hour and with a benzene/($C_9$-$C_{16}$ linear olefin) mole ratio in the range 1 to 20. Different temperatures can, of course, be employed in the two reaction zones, in the event when two separate reactors are used.

A particular implementation of an apparatus for carrying out the process of the invention is described in relation to the accompanying figure. It is not limiting in scope.

Fresh benzene arriving via a line 1 is mixed with benzene from the head of a first fractionation column 9 (line 10). This feed constituted by benzene is mixed with a stream comprising linear $C_9$-$C_{16}$ olefins, preferably $C_{10}$-$C_{14}$ linear olefins, and mainly $C_{10}$-$C_{14}$ paraffins (line 2). The overall mixture obtained constitutes the feed to an alkylation reactor 6. Said feed initially traverses a heat exchanger 3 where it is pre-heated by indirect heat exchange with an effluent from alkylation reactor 6. After passing through heat exchanger 3, the feed is sent to alkylation reactor 6 via a line 4. The alkylation reactor 6 is characterized in that it comprises two distinct reaction beds A and B, each containing a different catalyst. A second mixture constituted by at least linear $C_9$-$C_{16}$ olefins, preferably $C_{10}$-$C_{14}$ linear olefins, accompanied by mainly $C_{10}$-$C_{14}$ paraffins is introduced via line 5 directly into reactor 6, the injection point being located between the two catalyst beds A and B. At the outlet from reactor 6, the effluent is sent via line 7 to heat exchanger 3 then via a line 8 to a first fractionation column 9. At the head of said first fractionation column 9, the majority of the excess benzene that has not reacted is extracted and recycled via a line 10. A fraction is recovered from the bottom of this first fractionation column 9 and sent to a second fractionation column 12. Linear $C_9$-$C_{16}$ olefins, preferably $C_{10}$-$C_{14}$, that have not been transformed, and the paraffins initially present in the feed are mainly recovered from the head of this second fractionation column 12. At least a portion of this effluent can be recycled to the line supplying benzene to reactor 6. A mixture is recovered from the bottom of this second fractionation column 12, which is sent via a line 14 to a third fractionation column 15. A mixture of 2-phenylalkane, 3-phenylalkane, 4-phenylalkane, 5-phenylalkane and 6-phenylalkane is mainly recovered from the head of this third fractionation column 15 and sent to storage via a line 16. Dialkylbenzenes are mainly recovered from the bottom of this third fractionation column 15 via a line 17.

Examples 1 to 6 below do not limit the scope of the invention. They are given by way of illustration to provide the skilled person with a better understanding of the present invention.

EXAMPLE 1

Preparation of Catalyst A Based on Y Zeolite

The starting material was a NaY zeolite with formula $NaAlO_2(SiO_2)_{2.5}$. This zeolite underwent 5 successive exchanges in ammonium nitrate solutions at a concentration of 2M, at a temperature of 95° C. for a period of 2 hours and with a (volume of solution/weight of zeolite) ratio of 8 cm$^3$/g. The sodium content in the NH$_4$Y zeolite obtained was 0.9% by weight. This product was rapidly introduced into a furnace pre-heated to 770° C. and left for 4 hours in a static atmosphere. The zeolite then underwent an acid treatment under the following conditions: the ratio between the volume of 3 N nitric acid and the weight of solid was 0.9 cm$^3$/global; the temperature was 95° C. and the treatment period was 3 hours. A further treatment was then carried out under the same conditions, but with a 0.5 N nitric acid solution. The zeolite obtained had a sodium content of 0.1% by weight and a Si/Al atomic ratio of 24. The zeolite was formed by extrusion with alumina (80% Y zeolite and 20% alumina). The extrudates were then dried and calcined at 550° C.

EXAMPLE 2

Preparation of Catalyst B Based on Mordenite Zeolite (MOR)

The starting material was a mordenite zeolite in its sodium form with chemical formula (anhydride form) $NaAlO_2(SiO_2)_{5.1}$ and a sodium content of 5% by weight. 100 grams of this powder was heated under reflux to 100° C. for 2 hours in a solution of 4M ammonium nitrate with a (volume of solution/weight of zeolite) ratio of 4 cm$^3$/g. This cation exchange operation was repeated 3 times. The sodium content in the NH$_4$MOR zeolite was about 500 ppm (parts per million). The zeolite then underwent an acid attack using an aqueous 4.5N nitric acid solution: the zeolite was heated under reflux in this aqueous solution for 2 hours with a (volume of HNO$_3$/weight of zeolite) ratio of 4 cm$^3$/g. After this treatment, the zeolite was washed with demineralized water. The mordenite obtained had a Si/Al atomic ratio of 40 and a sodium content of 20 ppm by weight. It was then mixed with an alumina gel (80% by weight mordenite and 20% by weight alumina gel). The mixture obtained was formed into extrudates with a diameter of about 1.8 mm by passing through a die. The extrudates were then oven dried at 120° C. overnight and calcined in dry air at 550° C.

EXAMPLE 3

Alkylation of Benzene by 1-dodecene- in the Presence of Catalyst A Based on Y Zeolite (Not in Accordance With the Invention)

A reactor containing 50 cm$^3$ of catalyst A in the form of extrudates prepared as described in Example 1 was used.

The operating conditions for alkylating benzene by 1-dodecene were as follows:
temperature: 135° C.;
pressure: 4 MPa;

HSV=1 h$^{-1}$ (cm$^3$ (benzene+1-dodecene) feed/cm$^3$ of catalyst/hour);

Benzene/1-dodecene mole ratio: 5.5.

A feed was prepared containing 72% by weight of benzene and 28% by weight of 1-dodecene. The results obtained are shown in Table 2.

TABLE 2

| | |
|---|---|
| conversion of 1-dodecene (%) | 99.2 |
| Composition of product obtained (wt %) | |
| 2-phenylalkane | 26.2 |
| 3-phenylalkane | 21 |
| 4-phenylalkane | 18.9 |
| 5-phenylalkane | 11 |
| 6-phenylalkane | 10.9 |
| didodecylbenzene | 11 |
| heavy residue | 1 |

The proportion of 2-phenylalkane in the mixture constituted by 2-phenylalkane, 3-phenylalkane, 4-phenylalkane, 5-phenylalkane and 6-phenylalkane was 29.5%. The monoalkylated products represented 88% by weight of the total composition from the alkyl reaction carried out with a catalyst based on a Y zeolite.

EXAMPLE 4

Alkylation of Benzene by 1-dodecene- in the Presence of Catalyst B Based on Mordenite (Not in Accordance With the Invention)

Again, a reactor containing 50 cm$^3$ this time of catalyst B in the form of extrudates prepared as described in Example 2 was used. The test described in Example 3 was carried out under the same operating conditions and with the same feed. The results obtained are shown in Table 3.

TABLE 3

| | |
|---|---|
| conversion of 1-dodecene (%) | 98.7 |
| Composition of product obtained (wt %) | |
| 2-phenylalkane | 77.2 |
| 3-phenylalkane | 11 |
| 4-phenylalkane | 1.5 |
| 5-phenylalkane | 0.2 |
| 6-phenylalkane | 0 |
| didodecylbenzene | 9.6 |
| heavy residue | 0.5 |

The proportion of 2-phenylalkane in the mixture constituted by 2-phenylalkane, 3-phenylalkane, 4-phenylalkane, 5-phenylalkane and 6-phenylalkane was 85.9%. The monoalkylated products represented 89.9% by weight of the total composition from the alkyl reaction carried out with a catalyst based on mordenite.

EXAMPLE 5

(In Accordance With the Invention): Alkylation of Benzene by 1-dodecene- in Two Reactors Mounted in Series An apparatus comprising two distinct reactors was used. In accordance with the process of the present invention, 30 cm$^3$ of catalyst A based on Y zeolite was used in a first bed in the first reactor, and 20 cm$^3$ of catalyst B based on mordenite was used in a second bed in the second reactor, the selectivity for monoalkylated products of catalyst A being lower than that of catalyst B. A feed was prepared containing 84% by weight of benzene and 16% by weight of 1-dodecene. This feed was injected into the inlet to the first reactor containing catalyst A. Pure 1-dodecene was also injected between the two reactors. Benzene was injected into the inlet to the first reactor at a flow rate of 34.5 cm$^3$/h and 1-dodecene at a flow rate of 9.3 cm$^3$/h. All of the effluent leaving the first reactor and 1-dodecene at a flow rate of 6.2 cm$^3$/h were injected into the inlet to the second reactor. The first reactor thus functioned with a benzene/1-dodecene flow rate of 10.5.

The experimental conditions were as follows:

temperature of the two reactors: 135° C.;

pressure: 4 MPa;

overall HSV over the two reactors: 1 h$^{-1}$ (expressed as cm$^3$ of feed (benzene+1-dodecene) /cm$^3$ of catalyst/ hour);

The results obtained are shown in Table 4. The compositions indicated are those determined at the outlet from the second reactor.

TABLE 4

| | |
|---|---|
| conversion of 1-dodecene (%) | 99.1 |
| Composition of product obtained (wt %) | |
| 2-phenylalkane | 49.9 |
| 3-phenylalkane | 17.6 |
| 4-phenylalkane | 11.1 |
| 5-phenylalkane | 6.9 |
| 6-phenylalkane | 7 |
| didodecylbenzene | 7.1 |
| heavy residue | 0.4 |

The proportion of 2-phenylalkane in the final mixture constituted by 2-phenylalkane, 3-phenylalkane, 4-phenylalkane, 5-phenylalkane and 6-phenylalkane was 54%. The monoalkylated products represented 92.5% by weight of the total composition from the alkylation reaction.

It can also be seen that using the two catalysts substantially increased the selectivity for monophenylalkanes (monoalkylated products) by reducing the quantity of dialkylated compounds and heavy polyalkylated compounds.

EXAMPLE 6

(Comparative): Alkylation of Benzene by 1-dodecene- in Two Reactors Mounted in Series A combination of two catalysts was used: the catalyst used in the first bed was catalyst B based on mordenite zeolite as described above; the catalyst used in the second bed was a catalyst based on silica-alumina sold by Condea under the trade name Siralox 40. To determine the selectivity of the catalyst based on silica-alumina for monoalkylated product when it is used to alkylate benzene by 1-dodecene, a test similar to that described in Example 3 was carried out under the same operating conditions. After the reaction, the 1-dodecene conversion was 100% and the proportion of monoalkylated products in the mixture constituted by the monoalkylated compounds, dialkylated compounds and heavy residues was 68.5%. The selectivity for monoalkylated products of the, catalyst based on silica-alumina was thus lower than that for catalyst B based on mordenite used in the first catalytic bed.

To carry out the reaction for alkylating benzene by 1-dodecene in the presence of two catalysts as described above, an apparatus comprising two distinct reactors was used. 30 cm³ of catalyst B based on mordenite was used in a first bed in a first reactor, and 20 cm³ of Siralox 40 (silica-alumina) catalyst was used in a second bed in a second reactor.

A feed was prepared containing 84% by weight of benzene and 16% by weight of 1-dodecene. This feed was injected into the inlet to the first reactor containing catalyst B. Pure 1-dodecene was also injected between the two reactors. Benzene was injected into the inlet to the first reactor at a flow rate of 34.5 cm³/h along with 1-dodecene at a flow rate of 9.3 cm³/h. All of the effluent leaving the first reactor was injected into the inlet to the second reactor along with 1-dodecene at a flow rate of 6.2 cm³/h. Thus, the first reactor functioned with a benzene/1-dodecene mole ratio of 10.5.

The experimental conditions were as follows:
temperature of the two reactors: 135° C.;
pressure: 4 MPa;
overall HSV over the two reactors: 1 h⁻¹ (expressed as cm³ of feed (benzene+1-dodecene) /cm³ of catalyst/ hour);

The results obtained are shown in Table 5. The compositions indicated are those determined at the outlet from the second reactor.

TABLE 5

| | |
|---|---|
| conversion of 1-dodecene (%) | 100 |
| Composition of product obtained (wt %) | |
| 2-phenylalkane | 46.3 |
| 3-phenylalkane | 15.2 |
| 4-phenylalkane | 10.0 |
| 5-phenylalkane | 6.2 |
| 6-phenylalkane | 3.5 |
| didodecylbenzene | 15.6 |
| heavy residue | 3.2 |

The proportion of 2-phenylalkane in the final mixture constituted by 2-phenylalkane, 3-phenylalkane, 4-phenylalkane, 5-phenylalkane and 6-phenylalkane was 57%. The monoalkylated products represented 81.2% by weight of the total composition from the alkylation reaction.

The combination of the two catalysts disposed in such a manner that the selectivity for monoalkylated products of the catalyst in the first reactor was higher than that of the catalyst in the second reactor allowed the amount of 2-phenylalkane to be adjusted to a value of close to that obtained by a combination of two catalysts in accordance with the process of the invention, i.e., disposed so that the selectivity for monoalkylated products of the catalyst occupying the first reactor was lower than that of the catalyst in the second reactor. In contrast, the process of the invention resulted in a substantial improvement in the yield of monoalkylated products (92.5% by weight as opposed to 81.2% by weight) to the detriment of the production of di-alkylated compounds and heavy polyalkylated compounds (7.5% as opposed to 18.8% in the comparative example).

The invention claimed is:

1. A process for producing phenylalkanes comprising alkylating at least one aromatic compound by at least one linear olefin containing 9 to 16 carbon atoms per molecule carried out in the presence of at least two different catalysts and used in at least two distinct reaction zones, the selectivity for monoalkylated products of the catalyst contained in the first reaction zone being lower than that of the catalyst contained in the second reaction zone located downstream of the first reaction zone in the direction of fluid movement.

2. A process for producing phenylalkanes according to claim 1, in which at least one of said catalysts contained in said reaction zones comprises at least one zeolite.

3. A process for producing phenylalkanes according to claim 2, in which the zeolite is selected from the group formed by consisting of zeolites with structure types FAU, MOR, MTW, OFF, MAZ, BEA and EUO.

4. A process for producing phenylalkanes according to claim 3, in which the zeolite is a zeolite with structure type FAU.

5. A process for producing phenylalkanes according to claim 4, in which the zeolite is a Y zeolite.

6. A process for producing phenylalkanes according to claim 3, in which the zeolite is a zeolite with structure type MOR.

7. A process for producing phenylalkanes according to claim 6, in which the zeolite is a mordenite zeolite.

8. A process for producing phenylalkanes according to claim 1, in which the two catalysts are zeolitic catalysts.

9. A process for producing phenylalkanes according to claim 8, in which the zeolites contained in each of the different zeolitic catalysts differ from each other in their structure type and/or in the chemical composition of their crystalline framework.

10. A process for producing phenylalkanes according to claim 8, in which the zeolitic catalyst of the first reaction zone contains a Y zeolite and the zeolitic catalyst in the second reaction zone contains a mordenite zeolite.

11. A process for producing phenylalkanes according to claim 1, in which the olefin is mixed with the aromatic compound upstream of the first reaction zone.

12. A process for producing phenylalkanes according to claim 1, in which a first fraction of the olefin is mixed with the aromatic compound upstream of the first catalytic zone and in which a second fraction of the olefin is mixed with at least a portion of the effluents from the first reaction zone.

13. A process for producing phenylalkanes according to claim 12, in which the quantity of olefin contained in said first fraction is such that substantially all of the olefin is consumed in the first reaction zone.

14. A process for producing phenylalkanes according to claim 1, in which said alkylation reaction is followed by at least one step for separating the excess reactants.

15. A process for producing phenylalkanes according to claim 1, in which said alkylation reaction is followed by at least one step for separating monoalkylated compounds deriving from the reaction.

16. A process for producing phenylalkanes according to claim 1, in which the linear olefin is an olefin containing 10 to 14 carbon atoms per molecule.

17. A process for producing phenylalkanes according to claim 1, in which the linear olefin is 1-dodecene.

18. A process according to claim 1, further comprising suiphonating the obtained phenylalkane to produce a detergent.

* * * * *